(12) United States Patent
Seidler

(10) Patent No.: US 8,537,967 B2
(45) Date of Patent: Sep. 17, 2013

(54) SHORT WORKING DISTANCE SPECTROMETER AND ASSOCIATED DEVICES, SYSTEMS, AND METHODS

(75) Inventor: Gerald Todd Seidler, Seattle, WA (US)

(73) Assignee: University of Washington, Seattle, WA (US)

( * ) Notice: Subject to any disclaimer, the term of this patent is extended or adjusted under 35 U.S.C. 154(b) by 281 days.

(21) Appl. No.: 12/879,922

(22) Filed: Sep. 10, 2010

(65) Prior Publication Data

US 2011/0058652 A1 Mar. 10, 2011

Related U.S. Application Data

(60) Provisional application No. 61/241,366, filed on Sep. 10, 2009.

(51) Int. Cl.
| | | |
|---|---|---|
| *G01N 23/223* | (2006.01) | |
| *G01N 23/20* | (2006.01) | |
| *G01T 1/36* | (2006.01) | |
| *G21K 1/06* | (2006.01) | |

(52) U.S. Cl.
USPC ............. 378/45; 378/44; 378/71; 378/82; 378/83; 378/85

(58) Field of Classification Search
USPC .............. 378/44–50, 71–76, 82–85
See application file for complete search history.

(56) References Cited

U.S. PATENT DOCUMENTS

| | | | |
|---|---|---|---|
| 2,511,152 A | 6/1950 | Ekstein et al. | |
| 2,835,820 A | 5/1958 | Birks | |
| 2,842,670 A | 7/1958 | Birks | |
| 2,843,750 A | 7/1958 | Hillier | |
| 3,079,501 A | 2/1963 | Birks | |
| 3,927,319 A | 12/1975 | Wittry | |
| 3,963,439 A | 6/1976 | Birks et al. | |
| 3,989,944 A | 11/1976 | Birks et al. | |
| 4,016,456 A | 4/1977 | Birks et al. | |
| 4,131,794 A | 12/1978 | Bruninx | |
| 4,184,078 A | 1/1980 | Nagel et al. | |
| 4,798,446 A * | 1/1989 | Hettrick | 359/570 |
| 4,808,821 A | 2/1989 | Feuerbaum et al. | |
| RE33,992 E | 7/1992 | Nagel et al. | |
| 5,345,493 A | 9/1994 | D'Achard Van Enschut et al. | |
| 5,450,463 A * | 9/1995 | Iketaki | 378/43 |
| 5,509,043 A * | 4/1996 | Van Der Sluis | 378/85 |
| 5,802,137 A * | 9/1998 | Wilkins | 378/85 |
| 6,014,423 A * | 1/2000 | Gutman et al. | 378/85 |

(Continued)

OTHER PUBLICATIONS

Huotari, S. et al., "Resonant inelastic hard x-ray scattering with diced analyzer crystals and position-sensitive detectors," Review of Scientific Instruments 77, 053102-1 (2006), 7 pages.

(Continued)

*Primary Examiner* — Allen C. Ho
(74) *Attorney, Agent, or Firm* — Christensen O'Connor Johnson Kindness PLLC

(57) ABSTRACT

A spectrometer includes a rigid body having a first planar face with an orientation and a second planar face with a different orientation than the first planar face. The first and second planar faces are configured to position Bragg diffraction elements, and the orientation of the first planar face and the different orientation of the second planar face are arranged to convey a predetermined spectral range of the electromagnetic radiation to non-overlapping regions of the sensor location via the diffraction elements.

14 Claims, 4 Drawing Sheets

(56) References Cited

U.S. PATENT DOCUMENTS

| | | | |
|---|---|---|---|
| 6,041,099 A * | 3/2000 | Gutman et al. | 378/85 |
| 6,049,588 A * | 4/2000 | Cash, Jr. | 378/85 |
| 6,226,347 B1 * | 5/2001 | Golenhofen | 378/45 |
| 6,233,096 B1 * | 5/2001 | Marcelli et al. | 359/574 |
| 6,510,200 B1 * | 1/2003 | Martynov et al. | 378/84 |
| 6,574,306 B2 * | 6/2003 | Kikuchi | 378/84 |
| 6,628,748 B2 * | 9/2003 | Michaelsen et al. | 378/44 |
| 6,804,324 B2 * | 10/2004 | Martynov et al. | 378/36 |
| 7,035,374 B2 * | 4/2006 | Chen | 378/84 |
| 7,039,160 B2 * | 5/2006 | Hoheisel | 378/84 |
| 7,075,073 B1 | 7/2006 | Janik et al. | |
| 7,184,583 B2 * | 2/2007 | Ritter et al. | 382/132 |
| 7,236,566 B2 * | 6/2007 | Gibson et al. | 378/71 |
| 7,356,114 B2 * | 4/2008 | Kataoka et al. | 378/44 |
| 8,204,174 B2 * | 6/2012 | Connor et al. | 378/62 |
| 2002/0044626 A1 | 4/2002 | Verman et al. | |
| 2004/0151631 A1 | 8/2004 | Rigler | |
| 2006/0060189 A1 | 3/2006 | Liu et al. | |
| 2006/0153332 A1 | 7/2006 | Kohno et al. | |
| 2009/0174989 A1 | 7/2009 | Nagel et al. | |
| 2009/0205398 A1 | 8/2009 | Nagel et al. | |

OTHER PUBLICATIONS

Huotari, S. et al., "Improving the performance of high-resolution X-ray spectrometers with position-sensitive pixel detectors," Journal of Synchrotron Radiation 12 (2005), pp. 467-472.

Hayashi, H. et al., "A multi-crystal spectrometer with a two-dimensional position-sensitive detector and contour maps of resonant Kβ emission in Mn compounds," Journal of Electron Spectroscopy and Related Phenomena 136 (2004), pp. 191-197.

Hayakawa, S. et al., "A wavelength dispersive X-ray spectrometer for small area X-ray fluorescence spectroscopy at SPring-8 BL39XU," Spectrochimica Acta Part B 24 (1999), pp. 171-177.

Hayakawa, S. et al., "High Resolution X-Ray Fluorescence Measurements Using a Flat Analyzer Crystal and an X-Ray CCD," J. Trace and Microprobe Techniques 19(4) (2001), pp. 615-621.

Collart, E. et al., "Spherically bent analyzers for resonant inelastic X-ray scattering with intrinsic resolution below 200 meV," Journal of Synchrotron Radiation 12 (2005), pp. 473-478.

Nagel, D. J., "Simple multiple-crystal x-ray spectrograph," Review of Scientific Instruments 54, 12 (1983), pp. 1797-1798.

Hill, K.W. et al., "A spatially resolving x-ray crystal spectrometer for measurement of ion-temperature and rotation-velocity profiles on the Alcator C-Mod tokamaka)," Review of Scientific Instruments 79, 10E320 (2008), 4 pages.

Gilfrich, J. V. et al., "X-Ray Spectrometry for Particulate Air Pollution—A Quantitative Comparison of Techniques," Analytical Chemistry 45, 12 (1973), 8 pages.

Dumond, J. W. M. et al., "The Multiple Crystal X-Ray Spectrograph," Review of Scientific Instruments 1, 88 (1930), 18 pages.

Baronova, E. et al, "Three-channel x-ray crystal spectrometer for diagnosing high energy density plasmas," Review of Scientific Instruments 77, 103104 (2006), 5 pages.

* cited by examiner

US 8,537,967 B2

SHORT WORKING DISTANCE SPECTROMETER AND ASSOCIATED DEVICES, SYSTEMS, AND METHODS

CROSS-REFERENCE TO RELATED APPLICATIONS

This application claims priority to and the benefit of co-pending U.S. provisional patent application Ser. No. 61/241,366, filed Sep. 10, 2009, which application is incorporated herein by reference in its entirety.

TECHNICAL FIELD

The present invention is directed generally to X-ray spectrometry systems, and in particular, but not necessarily exclusively to a multiple element short working distance spectrometer.

BACKGROUND

Spectrometry systems can be used to confirm the presence of or to determine the concentration, electronic or magnetic properties, or local chemical environment of a given chemical species in a sample, such as in physical or analytical chemistry. Two common spectroscopy methods are absorption spectrometry and fluorescence spectrometry. In absorption spectrometry, a beam of light is sent through a sample to be analyzed, and certain wavelengths of the light are absorbed by the sample. By comparing the wavelengths of the absorbed light to known chemical absorption spectra, the components of the sample may be identified. In fluorescence spectrometry, a sample is bombarded by high energy light or other radiation capable of inducing electronic transitions to higher energy levels. As the excited electrons fall back to lower energy levels, the wavelength of the emitted light can be used to identify numerous atomic-scale properties of the sample.

The Rowland circle and either the Johann or Johannson geometries can be employed in spectrometry systems. In this arrangement, a curved, crystal-based (e.g., silicon or germanium) diffraction element is used for wavelength-specific focusing of X-rays. For applications involving higher-energy X-rays, a radius of curvature of one meter or more is typically required. This in turn creates a large working distance (which is a function of the radius of curvature) that results in a poor collection solid angle and creates the need for precision tolerances with little margin for error during fabrication, calibration, and operations. Further, every time such a device is moved, it must be calibrated to these tolerances, meaning that use of these devices can be expensive and time consuming. Similar considerations apply to the von Hamos geometry, which makes use of a simpler cylindrical design with only partial focusing properties.

BRIEF DESCRIPTION OF THE DRAWINGS

The objects and features of the invention can be better understood with reference to the drawings described below and the claims. The drawings are not necessarily to scale.

DETAILED DESCRIPTION

Figure 1A:
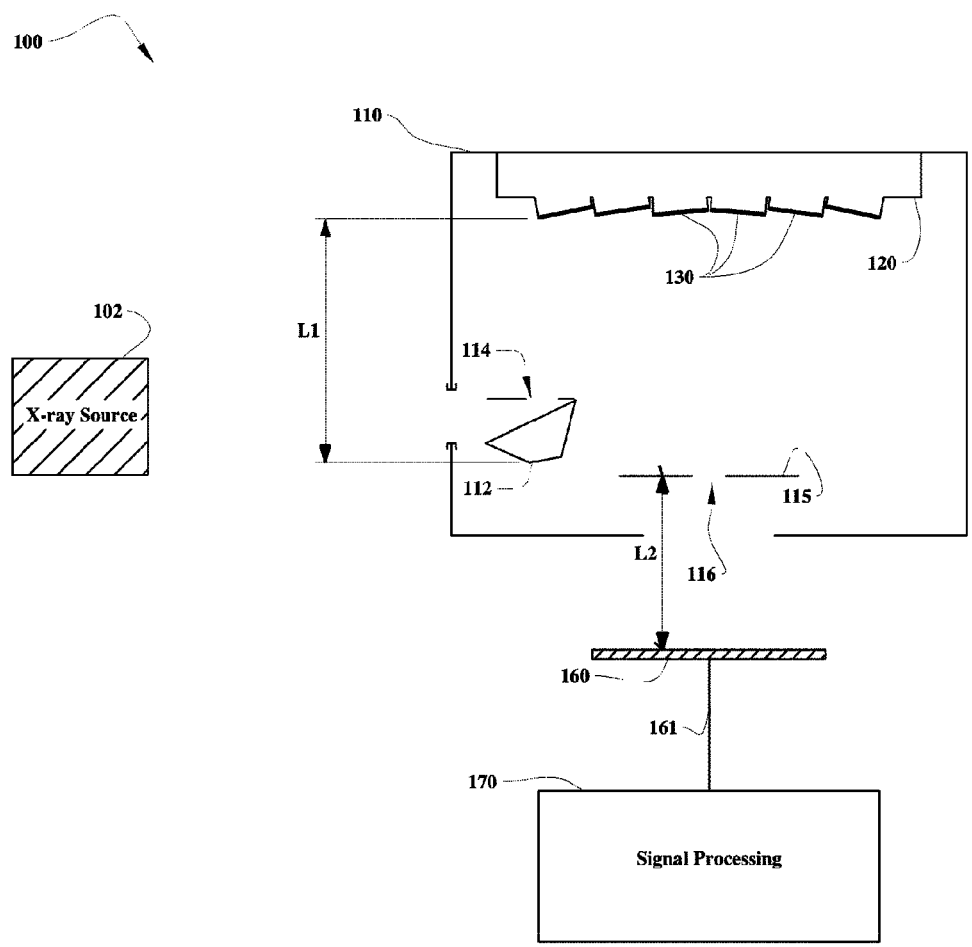
FIG. 1A is a schematic diagram of a system for conducting short working distance spectrometry.

The following examples, references and description provide specific details sufficient for a thorough understanding of embodiments of the disclosure. One skilled in the art will understand, however, that the disclosure may be practiced without certain details. In other instances, well known structures and functions have not been shown or described in detail to avoid unnecessarily obscuring the description of embodiments of the disclosure.

As used herein, the term "orientation" refers to the unit normal vector defining a planar face. For example, two planar faces with identical unit normal vectors have the same orientation, despite being in different locations.

As used herein, the term "planar face" refers to the single two dimensional surface of an object. For example, the planar face of a cubic-shaped diffraction crystal includes the two dimensional surface facing an X-ray source but does not include the surface of the 5 other faces of the cubic-shaped crystal. As used herein, the term planar refers to a generally flat surface. However, in some embodiments, planar can include weakly bent or slightly curved surfaces or substantially planar surfaces with localized regions of bending, curvature, or damage.

As used herein, the term "X-ray" refers to the band of the electromagnetic spectrum that extends from 0.01 nm to 10 nm in wavelength and 120 eV to 120 keV in energy. In one embodiment, the X-ray energy range extends from about 3 keV to 10 keV in energy. In general, embodiments of spectrometers and spectrometry systems can employ a variety of X-ray energy ranges. Moreover, embodiments of spectrometers and spectrometry systems can be configured for high energy resolution. For example, embodiments of spectrometers and spectrometry systems can have high energy resolution on the order of 1 eV or higher.

Briefly, the invention is directed to a short working distance spectrometer that is less expensive, smaller, more portable, and easier to fabricate and calibrate in comparison to current spectrometer systems. Embodiments of the spectrometer employ planar Bragg diffraction elements coupled to a rigid body, which can simplify fabrication and reduce cost relative to conventional spectrometers. In addition, embodiments of the spectrometer can be manufactured to be significantly smaller than conventional spectrometers, especially for higher energy X-rays at 1 eV or finer resolution (such conventional spectrometers having working distances on the order of 1 m or more). Embodiments of the spectrometer also employ other features, which offer a substantial improvement over conventional spectrometers, including reduced cost, easier fabrication, customization, and higher collection solid angles.

In one embodiment, the spectrometer includes a rigid body having a first planar face with an orientation and a second planar face with a different orientation than the first planar face. The first and second planar faces are configured to position Bragg diffraction elements, and the orientation of the first planar face and the different orientation of the second planar face are arranged to convey a predetermined spectral range (e.g., based in part on the orientation of the planar face) of the electromagnetic radiation to non-overlapping regions of the sensor location via the diffraction elements. In contrast to conventional spectrometers, and in particular, in contrast to conventional systems employing "diced" optics, embodiments of the spectrometer employ detection of non-overlapping regions of X-ray radiation. For example, not only do these spectrometers have a long working distance, they employ X-ray reflections that intentionally overlap at a detector.

Figure 1B:
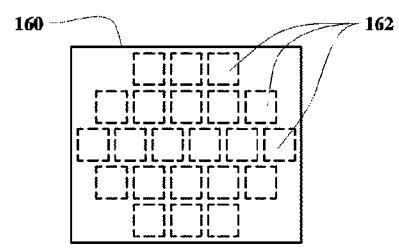
FIG. 1B is a top plan view of a sensor array employable in a system for conducting short working distance spectrometry.

FIG. 1A is a schematic diagram of a system 100 for conducting short working distance spectrometry. FIG. 1B is a top plan view of a sensor array employable in the system 100 and will be described in conjunction with FIG. 1A. The system 100 includes an X-ray source 102, a housing 110, a sample holder 112 disposed in the housing 110, an apparatus 120 disposed in the housing 110 for positioning Bragg diffraction elements 130, a sensor array 160, and a signal processing component 170 electrically coupled to the sensor array 160 via a signal path 161. In the configuration of FIG. 1A, the system 100 is generally considered to be in a short-working distance configuration because of the smaller dimensions employed relative to conventional spectrometry systems. For example, a distance L1 between the sample holder 112 and the apparatus 120 (or individual Bragg diffraction elements 130 or planar faces holding the Bragg diffraction elements) can be on the order of centimeters. In one embodiment, the dimension L1 can be in the range of about 1 to 15 cm.

The housing 110 further includes an entrance aperture 114, an exit spatial filter 115, and an exit aperture 116 located in the exit spatial filter 115. The entrance aperture 114 is typically on the order of several millimeters in diameter and allows fluorescence from a sample to enter while preventing or reducing stray scatter. The sample holder 112 is configured to hold samples to be scanned in a position and at an orientation so that the X-ray beam passes directly through the sample. In general, the position of the sample holder 112 relative to the other components of the system 100 may affect the energy range of the X-ray beam and the diffraction at the Bragg diffraction elements 130. The exit aperture 116 is positioned to filter the diffracted light from the diffraction elements 130, to prevent or reduce stray scatter from reaching the sensor array 160, and to select a predetermined range of diffracted electromagnetic radiation incident at the sensor array 160. The exit aperture 116, for example, may include an opening formed in a material that is opaque to X-ray radiation. In some embodiments, the housing 110 may be omitted from the system 100. For example, the sample holder 112, the entrance aperture 114, and/or the exit aperture 116 may each be arranged as stand-alone components that are not connected to the housing 110.

The sensor array 160 is spaced apart from the exit spatial filter 115 by a distance L2. The sensor array 160 is arranged to receive electromagnetic radiation and to output signals indicative of the spectrum of wavelengths (or equivalently of photon energies) associated with detected radiation. In one embodiment, for example, the sensor array 160 include a two-dimensional position-sensitive detector, such as, for example, a camera device or a diode array, that is arranged for detecting X-rays. FIG. 1B shows non-overlapping illumination of regions 162 of the sensor array 160. In some embodiments, there is an exclusive one-to-one correspondence between diffraction elements 130 and the non-overlapping regions 162 of the sensor array 160. In other embodiments, if the reflected radiation from different diffracting elements overlaps at certain sub-regions of the sensor array 160, such sub-regions can be excluded as necessary in subsequent signal processing. Also, while drawn as square-shaped in the figures, the non-overlapping regions 162 will generally have more complex shapes or profiles that can be different from one another in the sensor array 160 based on the overall geometry of the system 100.

Figure 3A:
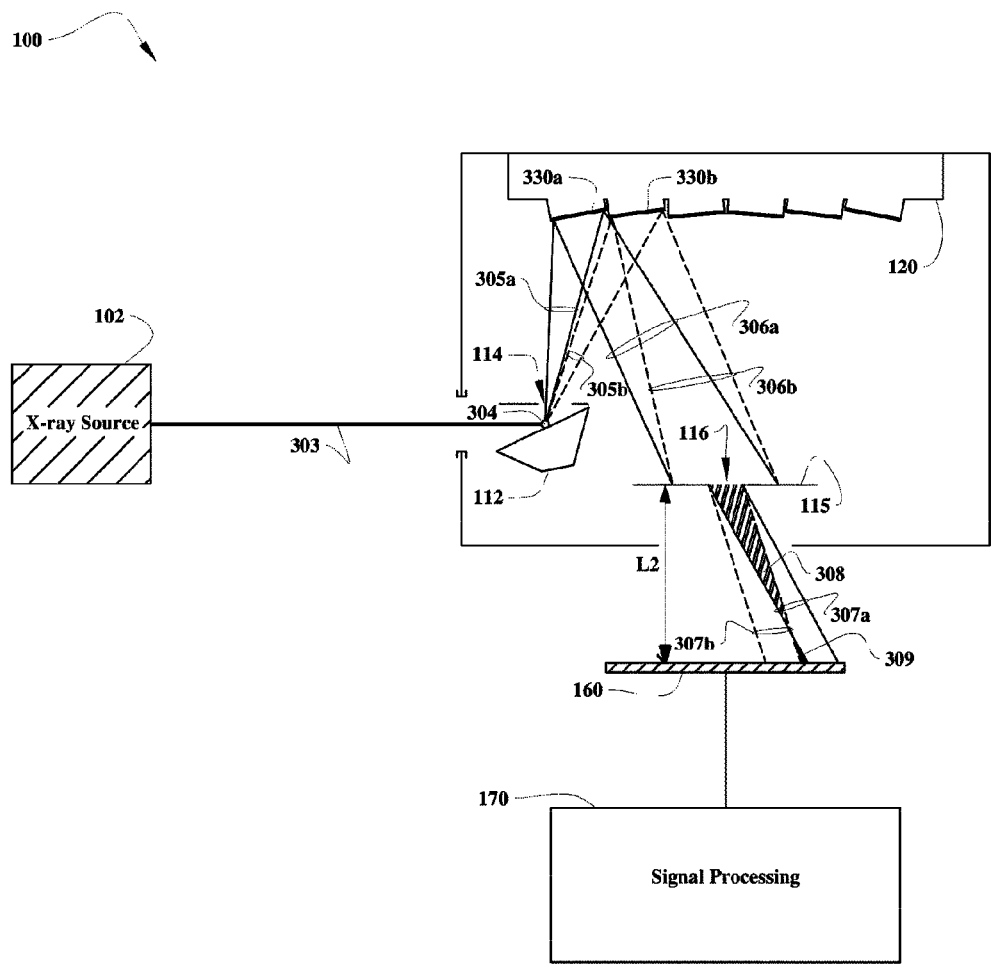
FIG. 3A is a schematic diagram showing paths of electromagnetic radiation in a spectrometry system.
Figure 3B:
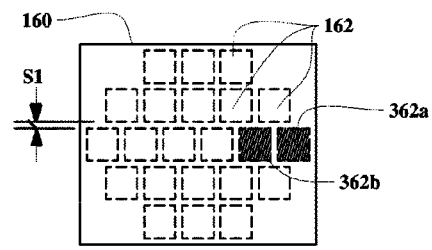
FIG. 3B is a top plan view of a sensor array partially illuminated by X-ray radiation.

The locations of the non-overlapping regions 162 can be defined, at least in part, by the configuration of the apparatus 120 and the exit aperture 116 (described further with reference to FIGS. 3A and 3B). The non-overlapping regions 162 of the sensor array 160 can be arranged to receive electromagnetic radiation and to output one or more output signals indicative of the intensities and locations of the received radiation. In some embodiments, the sensor array 160 may be flat, as shown in the figures, or may instead take a more complex shape, such as with tiled components on the surface of a cylinder.

Figure 4A:
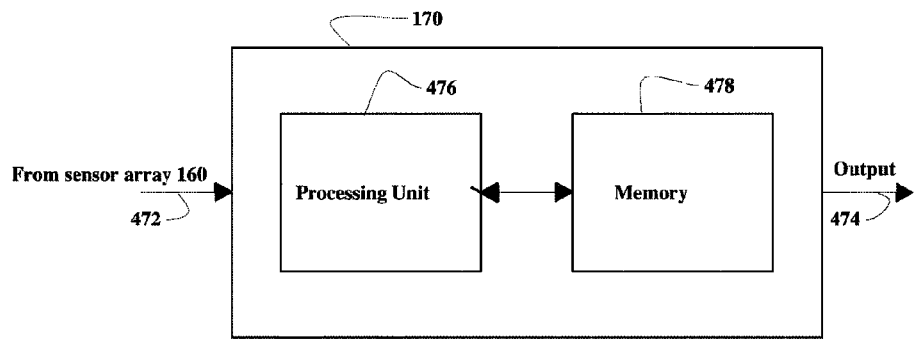
FIG. 4A is a schematic diagram of a signal processing component that can be employed in a spectrometry system.
Figure 4B:
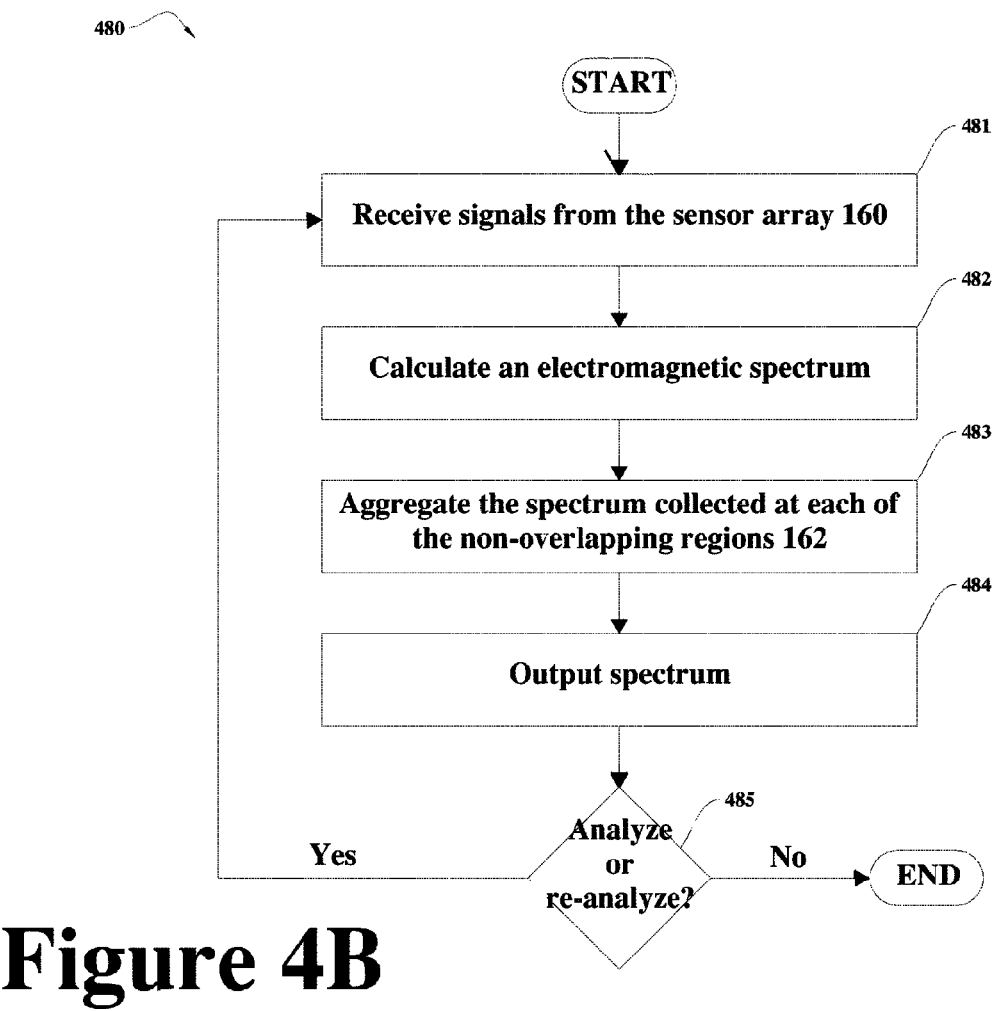
FIG. 4B is a flow diagram of a process for providing data indicative of an emission spectrum.

The signal processing component 170 is configured to receive the output signals from the sensor array 160 and to provide a variety of data indicative of the electromagnetic radiation 307a and 307b (described further with reference to FIGS. 4A and 4B).

Figure 2:
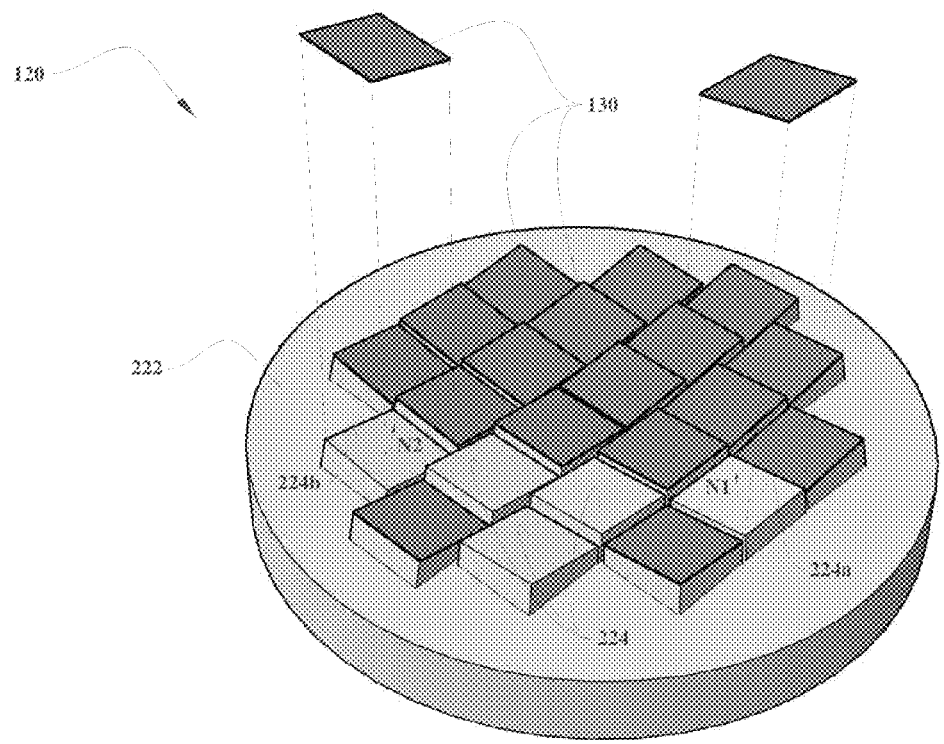
FIG. 2 is a partially exploded, isometric diagram of an apparatus for positioning Bragg diffraction components in a spectroscopy system.

FIG. 2 is a partially exploded, isometric diagram of the apparatus 120. The apparatus 120 includes a rigid body 222 and a plurality of planar faces 224 carried by the rigid body 222. The apparatus may be manufactured from a variety of materials. In some embodiments, the rigid body 222 includes a plastic material. In one embodiment, for example, the rigid body 222 may be manufactured by a machine that "prints" in three dimensions via additive manufacturing techniques. For example, RepRap (http://reprap.org/wiki/Mainpage) and Stratasys (http://www.stratasys.com/, based in Eden Prairie, Minn.) provide three-dimensional printers. In such embodiments, the apparatus 120 can be quickly fabricated. For example, a manufacturing engineer can design the apparatus using a computer aided design (CAD) program and create an output file that can be read by a three-dimensional file. In other embodiments, however, conventional subtractive manufacturing techniques, such as electric discharge machining and multi-axis computer-controlled mills, can be used to create the apparatus in several materials, including steel, aluminum, or other metallic materials and/or alloys.

The planar faces 224 are configured to position Bragg diffraction elements 130. The planar faces 224, for example, may have a surface area in the range of a few mm to 25 mm square. The Bragg diffraction elements 130 can be attached to the planar faces 224 via an adhesive, epoxy, or the like. The Bragg diffraction elements 130 can include a variety of materials having one or more compositional layers for diffracting electromagnetic radiation. Embodiments of the Bragg diffraction elements 130 include crystalline materials common in the semiconductor industry (e.g., silicon and/or germanium), other highly-crystalline materials (e.g., diamond, quartz, lithium fluoride, or beryl), and multi-layered materials (e.g., artificial multi-layers of silicon and molybdenum).

The orientations of the planar faces 224 are configured for directing electromagnetic radiation via the Bragg diffraction elements 130. For example, a first planar face 224a has an orientation N1 for directing a refracted X-ray towards the exit spatial filter 115 and ultimately one of the non-overlapping regions 162 of the sensor array 160 (see FIGS. 3A and 3B). Similarly, a second planar face 224b has a different orientation N2 for directing a refracted X-ray towards the exit spatial filter 115 and ultimately a different non-overlapping region of the sensor array 160. The orientation of the planar faces 224 may be solved as an inverse problem constrained by the desired spatial clearances around the sample 304, the distances L1 and L2, the location and dimensions of the exit spatial filter 115, the spatial resolution of sensor array 160, the desired energy resolution, and the location and dimensions of sensor array 160. This includes, but is not limited to, solutions based on the geometry required by the Rowland circle and either Johannson or Johann geometry, or by the von Hamos geometry. See, for example, the methods for orientating Bragg diffraction elements disclosed in the parent application, U.S. provisional application No. 61/241,366.

In one embodiment, the orientations of the planar faces 224 are configured to provide diffracted electromagnetic radiation with generally the same energy or wavelength range to the sensor array. For example, in such an embodiment, the Bragg diffraction elements 130 (when attached to the planar faces 224) and the exit spatial filter 115 (FIG. 1A) may be arranged to provide a generally similar range of energy to each of the non-overlapping regions 162.

In another embodiment, the orientations of the planar faces 224 are configured to provide diffracted electromagnetic radiation with different energy ranges. For example, the Bragg diffraction elements 130 (when attached to the planar faces 224) can each provide a different portion of an electromagnetic spectrum to different non-overlapping regions of the sensor array 160. In such an embodiment, the apparatus 120 can be configured for the detection of a specific sample with several different specific bands of emitted radiation. In such cases, the system 100 can be configured to include additional exit spatial filters for accommodating the different bands of emitted radiation.

FIG. 3A is a schematic diagram showing paths of electromagnetic radiation in the spectrometry system 100. FIG. 3B is a top plan view of the sensor array 160 and will be described in conjunction with FIG. 3A. To simplify the description, FIG. 3A only shows diffraction from two diffraction elements. In general, however, embodiments of the spectrometry system 100 can employ numerous diffraction elements for refracting numerous, non-overlapping paths of electromagnetic radiation at a sensor array.

The X-ray source 102 provides X-ray beam 303 to a sample 304 carried by the sample holder 112. The sample 304 emits electromagnetic radiation through the entrance aperture 114, as stimulated by the details of the incident radiation and the microscopic composition and structural details of the sample 304. A portion 305a of the electromagnetic radiation is incident onto a Bragg diffraction element 330a, and another portion 305b of the electromagnetic radiation is incident onto a Bragg diffraction element 330b. The Bragg diffraction elements 330a and 330b diffract electromagnetic radiation 306a and 306b towards the exit spatial filter 115. As discussed above, the direction of diffraction at individual Bragg diffraction elements is based on the orientation of the planar faces 224 of the apparatus 120 (see FIG. 2) and the choice of material and crystalline orientation of the respective diffraction elements 130.

The exit spatial filter 115, in turn, receives and filters the electromagnetic radiation 306a and 306b to provide electromagnetic radiation 307a and 307b to the sensor array 160. The aperture 116 is generally configured to allow a portion of the electromagnetic radiation 306a and 306b to pass through the exit spatial filter 115 while substantially blocking the remaining portion of the electromagnetic radiation 306a and 306b. In particular, the exit aperture 116 is configured to direct the electromagnetic radiation 307a and 307b to non-overlapping regions of the sensor array 160. FIG. 3B shows the illuminated non-overlapping regions 362a and 362b corresponding to the electromagnetic radiation 307a and 307b, respectively.

As shown, the electromagnetic radiation 307a and 307b overlaps (at region 308) upon exiting the exit spatial filter 115. The electromagnetic radiation 307a and 307b, however, does not overlap (at region 309) when reaching the sensor 160. The locations of the region 308 and the region 309 can be controlled by the size of the aperture 116. For example, the exit spatial filter 115 will block less electromagnetic radiation as the size of the aperture is increased. If the aperture is too large, however, the region 309 will not exist and the non-overlapping regions 162 will not be spaced apart from one another.

The locations of the region 308 and the region 309 can also be controlled by the distance L2. Decreasing the distance L2 decreases the size of the region 309 and the spacing distance S1 between the non-overlapping regions 162. Increasing the distance L2 increases the size of the region 309 and the spacing distance S1 between the non-overlapping regions 162.

In some embodiments, the exit aperture 116 is configured to filter a predetermined energy range of the electromagnetic radiation 307a and 307b. A larger aperture, for example, will filter less electromagnetic radiation than a smaller aperture.

FIG. 4A is a schematic diagram of the signal processing component 170. The signal processing component 170 is arranged to output information corresponding to an emission spectrum. For example, the signal processing component can output information corresponding to an absorption spectrum or a fluorescence spectrum of a sample at the sample holder 112 (FIG. 1A).

In general, the signal processing component 170 may have a variety of configurations. For example, a personal computer may serve as the signal processing component 170 and may run one or more software applications in conjunction with various hardware for processing signals and outputting information, such as to a display, a printer, or the like. Alternatively, the signal processing component may be a standalone device or the like, including a microcontroller or other hardware device.

As shown in the figure, the signal processing component 170 is arranged to receive input signals from the sensor array 160 via one or more signal paths 472 from the sensor array 160 (FIG. 1A). The processing component 170 is further arranged to output signals via one or more signal paths 474 based on the electromagnetic radiation detected at the sensor array 160. In general, the signal processing component 170 employs a processing unit 476 and a memory 478. The memory 478 may include RAM, ROM, and the like to provide processor executable instructions for calibration, for storing data, for outputting data, and for performing various operations based on the input signals 472.

FIG. 4B is a flow diagram showing a process 480 for employing the signal processing component 170 to providing data indicative of an emission spectrum. The process 480 begins at block 481 where the signal processing unit receives signals from the sensor array 160. The signals can be voltage, current, charge, or optical signals representing time-varying information indicative of the spatial distribution of X rays incident at one or more of the non-overlapping regions 162. The non-overlapping regions 162 may each convey an image showing the spatial distribution of X-ray intensity incident on the sensor array 160.

The process 480 continues to block 482, where the signal processing component 170 calculates an electromagnetic spectrum based on the input signals from the sensor array 160. The signal processing component 170 may employ any one of a myriad of algorithms for determining a spectrum, including statistical inferential methods or other signal processing algorithms. The signal processing component 170 can also apply band-pass or other filters for pre-processing of signals from sensor array 160 or post-processing of the calculated spectrum.

The central aspect to be considered is the calibration of the sensor array 160, specifically the determination of the wavelength or energy of X-ray photons expected to be incident at each spatially resolved point on sensor array 160. In some cases, this can be obtained as a pure consequence of conventional ray-tracing analysis of the entire system 100. In some applications, however, this will be directly determined by use of reference radiation sources with known distributions of X-ray wavelengths (spectra). Such reference experiments will give highly reliable calibration of some subset of spatial subregions (e.g. pixels) on the sensor array 160. With such partial information, the entire sensor array 160 can then be reliably calibrated using interpolation methods, statistical inferential methods, or other standard numerical techniques.

The process 480 continues to block 483, wherein the signal processing component 170 aggregates the spectrum collected at each of the non-overlapping regions 162. For example, referring to FIG. 3A, the signal processing component 170 can aggregate the spectrum determined for each of the non-overlapping regions 362a and 362b. In one embodiment, the statistical accuracy of the detection can be enhanced by analyzing similar spectral ranges at each of the non-overlapping regions 162. In another embodiment, a spectral range is based on different spectral ranges detected at each of the non-overlapping regions 162. In other embodiments, the non-overlapping regions 162 may represent the same energy range but may not be combined, as the different regions give different spectral information as a consequence of polarization of the emitted electromagnetic radiation or other advanced physical phenomenon.

The process 480 continues to block 484, where a spectrum indicative of the sample is output. For example, the output can be provided at a display, stored in memory, or output to a printer. At decision block 485, processing can return to block 480 for analyzing another sample (or re-analyzing the sample). Alternatively, processing can terminate. It should be noted that the invention is not limited to the specific processing blocks or order thereof. For example, in some embodiments, aggregation at the block 483 can be performed prior to the calculation of the electromagnetic spectrum at block 482.

From the foregoing it will be appreciated that representative embodiments have been described for purposes of illustration. However, well known characteristics often associated with spectrometry systems have not been described to avoid unnecessarily obscuring the various embodiments. In addition, various modifications may be made to the various embodiments, including adding or eliminating various features. For example, while the apparatus 120 is shown as having multiple arrays of planar faces for a supporting Bragg diffraction elements, other embodiments of the apparatus 120 may only employ a single array. Also, the apparatus 120 may include more or fewer planar faces than those illustrated.

In some embodiments, the planar faces may be slightly non-planar such that the planar face have a weak bend or have a slight curvature. For example, it is contemplated that a weak bend or slight curve in the (slightly non-planar) face and/or corresponding Bragg diffraction element can enhance the diffraction of X-rays from a Bragg diffraction element. The apparatus 120 may also incorporate other modifications, such as to increase reflectivity of the diffracting elements by the application of appropriate strains. For example, the diffraction elements can be substantially strained, including being weakly bent or otherwise intentionally damaged to decrease crystallinity, so as to advantageously influence their integrated reflection efficiency.

Moreover, embodiments of the system 100 may include other modifications or components. For example, a variety of X-ray emitters may be used in lieu of the X-ray source 102 and the sample 304. The X-rays emanating from the X-ray emitter may, for example, be fluorescence excited by continuous or pulsed ionizing radiation such as X-rays or high energy charged particle beams, such as in an electron microscope, or may be the result of elastic or inelastic scattering of incident X-ray radiation. For example, an electron microscopy system may use embodiments the apparatus 120 in an imaging modality with extremely high spatial resolution (e.g., the imaging modality is sensitive to the local magnetic or chemical properties of a sample scanned by the electron beam). Alternatively, the X-ray emitter may itself be radioactive or can be artificially induced by several means. The X-ray emitter may itself constitute a high temperature plasma, such as in fusion experiments or some extrasolar bodies (such as studied by X-ray telescopes), where several physical effects induce fluorescence or other emission modes at X-ray wavelengths.

The invention claimed is:

1. An X-ray spectroscopy system, comprising:
an apparatus for positioning Bragg diffraction elements, comprising a rigid body that includes:
a first planar face having an orientation; and
a second planar face having a different orientation than the orientation of the first planar face,
wherein the first and second planar faces are configured to position Bragg diffraction elements, and wherein the orientation of the first planar face and the different orientation of the second planar face are arranged to convey a predetermined spectral range of electromagnetic radiation to non-overlapping regions of a sensor array via the Bragg diffraction elements; and
an exit spatial filter having an exit aperture configured to select electromagnetic radiation for the non-overlapping regions of the sensor array.

2. The system of claim 1, wherein the distance between a sample to be analyzed and at least one of the first and second planar faces is in the range of about 1 cm to 15 cm.

3. The system of claim 1, wherein the first planar face and the second planar face are arranged such that the non-overlapping regions receive generally the same energy range of electromagnetic radiation.

4. The system of claim 1, wherein the first planar face and the second planar face are arranged such that the non-overlapping regions receive different energy ranges of electromagnetic radiation.

5. The system of claim 1, further comprising a first Bragg diffraction element coupled to the first planar face and a second Bragg diffraction element coupled to the second planar face.

6. The system of claim 5, wherein the first Bragg diffraction element and the second Bragg diffraction element comprise a crystalline material.

7. The system of claim 6, wherein the crystalline material includes diamond, silicon, germanium, and/or lithium fluoride.

8. The system of claim 5, wherein the first Bragg diffraction element and the second Bragg diffraction element comprise a synthetic thin-film multi-layered material.

9. The system of claim 1, wherein the exit aperture is configured to filter a predetermined energy range of the electromagnetic radiation.

10. The system of claim 1, further comprising a sensor array arranged to receive electromagnetic radiation.

11. The system of claim 10, wherein the sensor array comprises a two-dimensional position sensitive detector.

12. The system of claim 10, further comprising a signal processing component configured to output a signal based on electromagnetic radiation detected at the sensor array.

13. The system of claim 12, wherein the signal processing component outputs information describing a spectrum for radiation emanating from a sample.

14. An electron microscopy system comprising the apparatus of claim 1.

* * * * *